(12) United States Patent
Samani

(10) Patent No.: US 10,064,971 B2
(45) Date of Patent: Sep. 4, 2018

(54) PREVENTATIVE SOLUTION AND METHOD OF USE

(71) Applicant: HighQ Services, LLC, Cedar Park, TX (US)

(72) Inventor: Babak Samani, Cedar Park, TX (US)

(73) Assignee: HighQ Services, LLC, Cedar Park, TX (US)

(*) Notice: Subject to any disclaimer, the term of this patent is extended or adjusted under 35 U.S.C. 154(b) by 0 days.

(21) Appl. No.: 15/228,792

(22) Filed: Aug. 4, 2016

(65) Prior Publication Data

US 2017/0028092 A1 Feb. 2, 2017

Related U.S. Application Data

(63) Continuation-in-part of application No. 14/822,011, filed on Aug. 10, 2015, which is a continuation-in-part of application No. 13/838,276, filed on Mar. 15, 2013, now Pat. No. 9,101,675, which is a continuation-in-part of application No. 13/005,533, filed on Jan. 12, 2011, now Pat. No. 8,815,788.

(60) Provisional application No. 61/296,356, filed on Jan. 19, 2010, provisional application No. 61/380,455, filed on Sep. 7, 2010.

(51) Int. Cl.
*A61L 9/14* (2006.01)
*A61L 9/01* (2006.01)
*A61L 2/22* (2006.01)
*A61L 9/012* (2006.01)

(52) U.S. Cl.
CPC .................... *A61L 9/14* (2013.01); *A61L 2/22* (2013.01); *A61L 9/01* (2013.01); *A61L 9/012* (2013.01); *A61L 2209/135* (2013.01); *A61L 2209/21* (2013.01)

(58) Field of Classification Search
CPC .................... A61L 9/14; A61L 9/01
See application file for complete search history.

(56) References Cited

U.S. PATENT DOCUMENTS

| | | | | |
|---|---|---|---|---|
| 4,636,328 A * | 1/1987 | Flynn | ..................... | B65D 51/28 206/568 |
| 4,773,562 A * | 9/1988 | Gueret | ................... | A45D 40/24 222/135 |
| 4,989,758 A * | 2/1991 | Keller | ............... | B05C 17/00506 222/137 |
| 5,234,719 A * | 8/1993 | Richter | .................. | A01N 37/02 134/22.14 |
| 7,285,255 B2 * | 10/2007 | Kadlec | ..................... | A61L 2/18 210/753 |
| 8,815,788 B2 * | 8/2014 | Osborn | .................... | A61L 2/22 510/191 |

(Continued)

FOREIGN PATENT DOCUMENTS

JP 2006342113 A * 12/2006

*Primary Examiner* — Nicole M Buie-Hatcher
*Assistant Examiner* — M. Reza Asdjodi

(57) ABSTRACT

A preventative solution includes an aqueous base, 1 wt % to 6 wt % titanium dioxide having an average particle size of not greater than 100 nm, 0.5 wt % to 20 wt % alcohol having 2 to 4 carbons, and 3 wt % to 15 wt % of a binding agent. The preventative solution can be dispersed using a fogger, for example, sequentially with an odor neutralizing solution or a dis

(56) References Cited

U.S. PATENT DOCUMENTS

| | | | |
|---|---|---|---|
| 2005/0139608 A1* | 6/2005 | Muehlhausen | B65D 81/3283 222/94 |
| 2005/0238732 A1* | 10/2005 | Lu | A01N 25/22 424/717 |
| 2006/0116309 A1* | 6/2006 | Lambotte | C11D 17/0052 510/302 |
| 2006/0293202 A1* | 12/2006 | Cate | C11D 17/041 510/235 |
| 2007/0167340 A1* | 7/2007 | Barthel | C11D 17/042 510/220 |
| 2008/0207481 A1* | 8/2008 | Meine | C11D 3/50 512/4 |
| 2010/0184855 A1* | 7/2010 | Bernhardt | A01N 25/30 514/529 |
| 2011/0177992 A1* | 7/2011 | Osborn | A61L 2/22 510/417 |
| 2017/0028092 A1* | 2/2017 | Samani | A61L 2/22 |

\* cited by examiner

PREVENTATIVE SOLUTION AND METHOD OF USE

CROSS-REFERENCE TO RELATED APPLICATION(S)

The present application is a continuation-in-part of U.S. application Ser. No. 14/822,011, filed Aug. 10, 2015, entitled "PREVENTATIVE SOLUTION AND METHOD OF USE," which is a continuation-in-part of U.S. application Ser. No. 13/838,276 (now U.S. Pat. No. 9,101,675), filed Mar. 15, 2013, entitled "PREVENTATIVE SOLUTION AND METHOD OF USE," which is a continuation-in-part of U.S. application Ser. No. 13/005,533 (now U.S. Pat. No. 8,815,788), filed Jan. 12, 2011, entitled "AEROSOL DEODORIZER," which claims priority from U.S. Provisional Patent Application No. 61/296,356, filed Jan. 19, 2010, entitled "BACTERIA COLONY GROWTH INHIBITOR IN EASILY APPLIED FORM," and claims priority from U.S. Provisional Patent Application No. 61/380,455, filed Sep. 7, 2010, entitled "NANODEX—A DISPENSING DEVICE CONTAINING A MATERIAL CAPABLE OF COMBATING NITROGENOUS MALODORS BY ADDITION ELIMIATION REACTION, SALT FORMATION AND SOLVENT-INDUCED MIGRATION," which applications are incorporated by reference herein in their entirety.

FIELD OF THE DISCLOSURE

This disclosure, in general, relates to solutions having deodorizing properties and, in particular, solutions having deodorizing properties that may be applied as an aerosol or fog.

BACKGROUND

From the dawn of the modern age many people have at one time or another contemplated ways to cope with or eliminate malodorous air or infectious contamination. A number of methods have been employed, including burning candles, use of incense, opening windows, use of fans, spraying fragrances or other masking agents, or any combination thereof. Such methods are generally ineffective and a nuisance to implement.

Odors are a particular annoyance and in closed small spaces. For example, people are increasingly spending time in cars, tracking contaminants in and out of cars, and eating in cars. In addition, air leaks from outside the car and can introduce malodors into the enclosed space within a car. Such malodors can accumulate within the car, making travel within the vehicle unpleasant.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
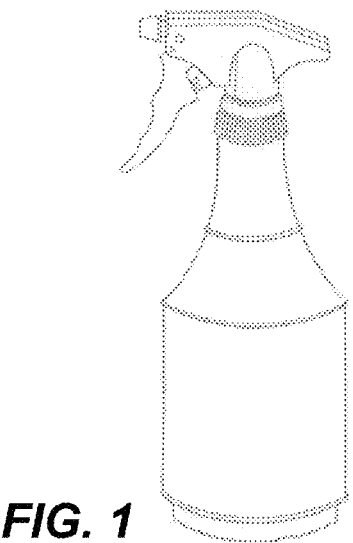
FIG. 1 includes an illustration of an exemplary spray bottle.

In an embodiment, a preventative solution includes a nano-sized titanium dioxide particulate and a binding agent dispersed in an aqueous solution. In an example, the binding agent is water-miscible and forms a coating upon drying. In another example, the binding agent is in the form of an emulsion. The solution may also include an alcohol, such as an ethyl alcohol or an isopropyl alcohol. In an example, the preventative solution can be applied in aerosol form or a fog.

In another embodiment, an odor neutralizing solution includes an aqueous base, an organic acid, a surfactant, an organic ester, and an ethylene glycol ether. Optionally, the solution can include a fragrance. In another example, the solution can include a dispersed polymer. The organic ester can be derived from a carboxylic acid having at least four carbons. The surfactant can be a nonionic surfactant or an anionic surfactant. An exemplary organic acid includes citric acid. The solution can be applied in aerosol form or as a fog.

In a first embodiment, a preventative solution can prevent or limit bacterial growth and can include an aqueous base, titanium dioxide, an alcohol, and a binding agent. As described in detail below, the aqueous solution can be sprayed or aerosolized and applied to a surface. Alternatively, the preventative solution can be applied with a cloth, sponge, or rag. Once applied to a surface, the preventative solution forms a preventative coating.

In an example, the preventative solution includes titanium dioxide particulate, such as microcrystalline titanium dioxide particulate. The titanium dioxide particulate may have an average primary particle size of 1 nanometer to 1000 nanometer, such as not greater than 100 nanometers. For example, the titanium dioxide particulate may have a primary particle size of not greater than 60 nanometers, such as not greater than 50 nanometers. Further, the titanium dioxide particulate may have an average particle size of at least 3 nanometers, such as at least 10 nanometers, or at least 30 nanometers. The solution may include the titanium dioxide particulate in an amount of 0.5 wt % to 30 wt % based on the weight of the preventative solution, such as an amount of 1 wt % to 6 wt %, an amount of 2 wt % to 6 wt %, or an amount of 3 wt % to 6 wt %.

In addition, the preventative solution may include an alcohol, such as a low molecular weight alcohol. For example, the alcohol may include an alcohol having between 2 and 6 carbons, such as between 2 and 4 carbons. In an example, the alcohol is ethanol. In another example, the alcohol is isopropyl alcohol. The alcohol may be present in the solution in an amount of 0.5 wt % to 20 wt % based on the total weight of the preventative solution, such as an amount of 0.5 wt % to 5 wt %, an amount of 0.5 wt % to 3 wt %, or amount of 0.5 wt % to 2 wt % based on the total weight of the preventative solution.

In addition, the preventative solution includes a binding agent. The binding agent can include a polymer or a wax. In an example, when the preventative solution is applied to a surface and the water evaporates, the binding agent may dry or cure, forming a coating on the surface and possibly securing the titanium dioxide to the surface. In an example, the binding agent is included in an amount of 1 wt % to 20 wt % based on the total weight of the preventative solution, such as an amount of 3 wt % to 15 wt %, 5 wt % to 15 wt %, 7 wt % to 15 wt %, or even 8 wt % to 15 wt % based on the total weight of the preventative solution. Alternatively, the binding agent can be included in an amount in a range of 0.5 wt % to 3 wt %, such as a range of 0.5 wt % to 2 wt %.

The polymer may be water-miscible polymer or may be emulsified within the aqueous base. An exemplary polymer includes polyethylene glycol, polypropylene glycol, polyvinyl chloride, polyvinyl acetate, partially-hydrolyzed polyvinyl acetate, ethylene vinyl acetate copolymer, polyvinyl alcohol, polyester such as polyethylene terephthalate (PET), polycarbonate, polyacrylate, acrylic esters, polyacrylonitrile, hydrolyzed polyacrylonitrile, polyolefin such as polyethylene, polypropylene, or blends or copolymers thereof, polyamide such as Nylon, polysiloxanes, polyurethane, a product of polyethylene diamine and adipic acid, fluoropolymer, or blends or copolymers thereof, or any combination thereof. For example, the polymer may be an acrylic polymer. In another example, the polymer is polyvinyl acetate. In a further example, the polymer is a silicone polymer. In another example, the polymer is polyurethane. In an additional example, the polymer is a polyamide. In a further example, the polymer is a polyvinyl chloride. In an additional example, the polymer is a poly alkyl glycol, such as polyethylene glycol or polypropylene glycol. Further, the polymer may be a polyolefin, such as polyethylene or polypropylene. An exemplary fluoropolymer can be formed of a homopolymer, copolymer, terpolymer, or polymer blend formed from a monomer, such as tetrafluoroethylene, hexafluoropropylene, chlorotrifluoroethylene, trifluoroethylene, vinylidene fluoride, vinyl fluoride, perfluoropropyl vinyl ether, perfluoromethyl vinyl ether, or any combination thereof. An exemplary fluoropolymer includes polytetrafluoroethylene (PTFE), a fluorinated ethylene propylene copolymer (FEP), a copolymer of tetrafluoroethylene and perfluoropropyl vinyl ether (perfluoroalkoxy or PFA), a copolymer of tetrafluoroethylene and perfluoromethyl vinyl ether (MFA), a copolymer of ethylene and tetrafluoroethylene (ETFE), a copolymer of ethylene and chlorotrifluoroethylene (ECTFE), polychlorotrifluoroethylene (PCTFE), poly vinylidene fluoride (PVDF), a terpolymer including tetrafluoroethylene, hexafluoropropylene, and vinylidenefluoride (THV), or any blend or any alloy thereof. In particular, the polymer dries or cures to form a UV transparent coating.

In another example, the binding agent includes a wax. For example, the wax can be a long chain fatty acid ester wax. The wax can have a melting point in a range of 35° C. to 75° C., such as a range of 35° C. to 50° C. In particular, the wax can be a sterol wax, such as a fatty acid ester of a sterol, e.g., lanolin. In another example, the wax can be a linear alcohol wax, such as cetyl palmitate.

Optionally, the preventative solution can include an emulsifier or surfactant, for example, in an amount of 0.1% to 10%, such as an amount of 0.3 wt % to 9 wt %, or 2 wt % to 8 wt %. The surfactant can be a nonionic surfactant, an anionic surfactant, a polymeric surfactant, a cationic surfactant, or any combination thereof. In a particular example, the surfactant includes a nonionic surfactant, such as an ethoxylate based surfactant. In another example, the surfactant can be a monoether of polyalkylglycol, such as a monoether of polyethylene glycol. In particular, the polyethylene glycol of the monoether can have between 3 and 24 ethylene glycol units, such as between 3 and 10, or between 3 and 5 ethylene glycol units. For example, the surfactant can be tetraethylene glycol monododecyl ether, pentaethylene glycol monododecyl ether, octaethylene glycol monododecyl ether, or a combination thereof.

In a further example, the preventative solution can include a solvent/emulsifier, such as dialkylammonium alkanoate, for example, diethylammonium acetate, which can act as to bind malodorous compounds such as tar, or solvate greasy compounds. The solvent can be included in an amount of 0.1% to 10% by weight, such as 0.5% to 10% by weight or 0.5% to 8% by weight.

The preventative solution may also include quaternary ammonium salts. An exemplary quaternary ammonium salts includes benzalkonium chloride, alkyl dimethyl benzyl ammonium chloride, alkyl alkoxyl diethylammonium dihydrogen phosphate, diallyl dimethyl ammonium acetate, or any combination thereof. The quaternary ammonium salt may be included in amount of not greater than 5 wt %, not greater than 4 wt %, or even not greater than 3 wt % based on the total weight of the preventative solution. For example, the quaternary ammonium salt can be included in an amount in a range of 0.1 wt % to 2 wt %, such as a range of 0.3 wt % to 1.0 wt %.

In addition, the preventative solution can include an antifungal agent. For example, the antifungal agent can be included in an amount of 0.01% to 5%, such as an amount of 0.01 wt % to 0.5 wt %, a range of 0.01 wt % to 0.1 wt %, or a range of 0.02 wt % to 0.7 wt % based on the total weight of the preventative solution. An exemplary antifungal agent can include an isothiazolinone agent, such as methylchloroisothiazolinone, methylisothiazolinone, or a combination thereof.

In a further example, the preventative solution can include an oxidizer. An exemplary oxidizer includes chlorine dioxide. The oxidizer can be included in an amount in a range of 0.05 wt % to 2 wt %, such as a range of 0.05 wt % to 1 wt %, or a range of 0.1 wt % to 0.5 wt %.

The preventative solution can have a near neutral pH. For example, the pH of the preventative solution can be in a range of 6 to 9, such as a range of 6.8 to 8, or even a range of 6.8 to 7.5. The preventative solution can optionally include pH control components, such as ammonium compounds or phosphates compounds, in an amount in a range of 0.1 wt % to 5 wt %.

The preventative solution is particularly beneficial for preventing odors associated with bacterial growth. While the preventative solution may additionally include fragrances or colorants, the preventative solution may consist essentially of an aqueous solution, a water-miscible or emulsified binding agent, the titanium dioxide particulate, and optionally a surfactant, which provide advantages associated with limiting bacterial growth, reducing malodors caused by bacteria particularly when the coating formed by such a solution is exposed to ultraviolet radiation. As such, the preventative solution is particularly well adapted for use in automobiles and other surfaces exposed to UV or sunlight.

In another embodiment, an odor neutralizing solution includes an aqueous base, an organic acid, a surfactant, an organic ester, and ethylene glycol ether. Optionally, the odor neutralizing solution can include a fragrance. In another example, the odor neutralizing solution may include a polymer. Such an odor neutralizing solution may also be used in spray or aerosol form and may be applied to surfaces.

In an example, the odor neutralizing solution includes an organic acid in an amount of 0.1 wt % to 10 wt % based on the total weight of the odor neutralizing solution. For example, the organic acid may be included in the solution in an amount of 0.1 wt % to 8 wt %, such as an amount of 0.5 wt % to 7 wt % or an amount of 4 wt % to 7 wt % based on the total weight of the odor neutralizing solution. In an alternative example, the organic acid may be included in the solution in an amount of 0.5 wt % to 3 wt % based on the total weight of the odor neutralizing solution. An exemplary organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof. In particular, the organic acid may be an alpha hydroxy carboxylic acid, such as a glycolic acid, lactic acid, citric acid, mandelic acid, maleic acid, tartaric acid, or any combination thereof. In a particular example, the organic acid includes citric acid.

The odor neutralizing solution can also include an organic ester in an amount of 0.1 wt % to 10 wt % based on the total weight of the odor neutralizing solution. For example, the organic ester may be included in an amount of 0.1 wt % to 8 wt %, such as an amount of 0.1 wt % to 3.5 wt %, an amount of 0.4 wt % to 3 wt %, or an amount of 0.7 wt % to 2 wt % based on the total weight of the odor neutralizing solution. In a particular example, the organic ester is a facile organic ester derived from a carboxylic acid having at least 4 carbons. For example, the carboxylic acid may include 4 to 16 carbons, such as 4 to 10 carbons, or 4 to 8 carbons. Further, the organic ester may be a methyl or ethyl ester of the carboxylic acid.

An exemplary organic ester includes methyl or ethyl butyrate, methyl or ethyl salicylate, methyl or ethyl valerate, methyl or ethyl amylate, ethyl or methyl hexanoate esters, or any combination thereof. Such organic esters may also be mixed with or alternatively include propanoate or acetate organic esters. In a particular example, the organic ester is an aliphatic organic ester, such as a butyrate or hexanoate organic ester. In particular, the organic ester may be a butyrate organic ester. In another example, the organic ester is an aromatic organic ester, such as a salicylate organic ester. Alternatively, the organic ester includes ethyl acetate or ethyl propanoate.

In addition to the organic ester or alternatively, the odor neutralizing solution can include an aldehyde, such as an alkyl-aldehyde, an aromatic aldehyde, a heterocyclic aldehyde, or any combination thereof. An alkyl-aldehyde is an alkane having an aldehyde functional group. An aromatic aldehyde includes benzyl or other cyclic carbon compounds including an aldehyde functional group. In a particular example, the aromatic aldehyde is a phenolic aldehyde, such as vanillin, cinnamaldehyde, cilantro, retinal, or any combination thereof. In an example, a heterocyclic aldehyde includes at least one heterocyclic ring and an aldehyde functional group. For example, a heterocyclic aldehyde includes pyridoxal.

In an example, the aldehyde can be used in conjunction with the above-identified organic esters. In another example, the aldehyde can be used in conjunction with propanoate or acetate organic esters. For example, the propanoate or acetate organic esters can be used in an amount described above in relation to the organic ester. The aldehyde, whether used in conjunction with an organic ester described above, the propanoate or acetate organic esters, or alone, can be used in an amount of not greater than 10 wt %, such as not greater than 5 wt %. For example, the aldehyde can be used in an amount of 0.1 wt % to 5 wt %, such as an amount of 0.3 wt % to 3 wt %, or an amount of 1 wt % to 3 wt %.

In a further example, the odor neutralizing solution includes a surfactant, such as in an amount of 0.1 wt % to 35 wt % based on the total weight of the odor neutralizing solution. For example, the surfactant may be present in an amount of 0.1 wt % to 10 wt %, such as an amount of 1 wt % to 10 wt %, an amount of 5 wt % to 10 wt %, or an amount of 6 wt % to 9 wt % based on the total weight of the odor neutralizing solution. Alternatively, the surfactant may be present in an amount of 1 wt % to 4 wt %, such as an amount of 1 wt % to 3 wt % based on the total weight of the odor neutralizing solution. Further, the surfactant may be included in amount relative to the organic ester, such as at a ratio of surfactant to organic ester in a range of 1:1 to 5:1, such as a range of 2:1 to 5:1, or even a range of 3:1 to 4:1.

In an example, the surfactant includes alpha olefin sulfonate (AOS), aliphatic ether sulfates (AES), alcohol sulfates (AS), linear alkylbenzenesulfonate (LAS), secondary alkyl sulfonate (e.g., Hostapur™ SAS 30), ethoxylated alcohols such as Neodol™ or Tamadol™, phenoxypolyethoxylethanol, such as octyl or nonyl phenoxypolyethoxylethanol (Tergitol™), alkyl ether phosphonate (e.g., Surfonic®), a phosphonate anionic surfactant, such as poly(oxy-1,2-ethanediyl) alpha-phosphono-omega-(methylphenoxy)-dipotassium (e.g., Rhodafac™ H66), natural surfactants, or any combination thereof. In an example, the surfactant is a nonionic surfactant, an anionic surfactant, a polymeric surfactant, a cationic surfactant or any combination thereof. In particular, the surfactant may be a nonionic surfactant. An exemplary nonionic surfactant includes ethylene oxide or propylene oxide derivatives, such as an ethoxylate ether surfactant. In a particular example, the surfactant includes phenoxypolyethoxylethanol, such as octyl or nonyl phenoxypolyethoxylethanol. In another example, the nonionic surfactant includes ethoxyl-propoxyl terpene, such as Rhodoclean™ EFC. In another example, the surfactant is an anionic surfactant. An exemplary anionic surfactant includes a sulfate or sulfonate surfactant. In an additional example, the surfactant is a natural surfactant, such as a naturally-derived decyl-glucoside sorbitan oleate crosspolymer. In a further example, the surfactant may be a cationic surfactant. Some cationic surfactants are effective at eliminating coliform bacteria or neutralize odors. An exemplary cationic surfactant includes soyethyl morpholinium ethosulfate.

In a further example, the odor neutralizing solution includes ethylene glycol ether, for example, in an amount of 0.1 wt % to 11 wt % based on the total weight of the odor neutralizing solution. In particular, the odor neutralizing solution may include the ethylene glycol ether in an amount of 0.5 wt % to 7 wt %, such as in an amount of 1.5 wt % to 5 wt %, or an amount of 1 wt % to 3 wt % based on the total weight of the odor neutralizing solution. The ethylene glycol ether does not include ethers of polyethylene glycols having more than two ethylene glycol units. For example, the ethylene glycol ether may have a single ethylene glycol unit. In a particular example, the ethylene glycol ether has a number of carbons in a range of 3 to 10, such as a range of 4 to 8, or a range of 4 to 6 carbons. An exemplary glycol ether includes ethylene glycol methyl ether, ethylene glycol ethyl ether, ethylene glycol butyl ether, ethylene glycol hexyl ether, or any combination thereof. Exemplary ethylene glycol ethers are commonly referred to as Cellosolve™.

The odor neutralizing solution may also include a polymer. In an example, the polymer may be polyethylene glycol, polypropylene glycol, polyvinyl chloride, polyvinyl acetate, partially-hydrolyzed polyvinyl acetate, ethylene vinyl acetate copolymer, polyvinyl alcohol, polyester such as polyethylene terephthalate (PET), polycarbonate, polyacrylate, acrylic esters, polyacrylonitrile, hydrolyzed polyacrylonitrile, polyolefin such as polyethylene, polypropylene, or blends or copolymers thereof, polyamide such as Nylon, polysiloxanes, polyurethane, a product of polyethylene diamine and adipic acid, or blends or copolymers thereof, or any combination thereof. For example, the polymer may be an acrylic polymer. In another example, the polymer is polyvinyl acetate. In a further example, the polymer is a silicone polymer. In a further example, the polymer is polyurethane. In an additional example, the polymer is a polyamide. In another example, the polymer is a polyvinyl chloride. In an additional example, the polymer is a poly alkyl glycol, such as polyethylene glycol or polypropylene glycol. Further, the polymer may be a polyolefin, such as polyethylene or polypropylene.

The polymer may be included in an amount not greater than 5 wt %, such as not greater than 3.5 wt %, not greater than 2.5 wt %, not greater than 2 wt %, or even not greater than 1.5 wt % based on the total weight of the odor neutralizing solution. In particular, the polymer may be included in an amount of at least 0.1 wt %, such as in a range of 0.1 wt % to 5 wt % based on the total weight of the odor neutralizing solution.

In a further example, the odor neutralizing solution can include an oxidizer. An exemplary oxidizer includes chlorine dioxide. The oxidizer can be included in an amount in a range of 0.01 wt % to 10 wt %, such as a range of 0.01 wt % to 1 wt %, a range of 0.01 wt % to 0.5 wt %, or a range of 0.02 wt % to 0.1 wt %.

In addition, the solution may include a fragrance. The fragrance may be included in an amount of not greater than 5 wt %, such as an amount of not greater than 2 wt %, not greater than 1 wt %, not greater than 0.7 wt %, or even not greater than 0.5 wt %. In a further example, the solution may include a colorant or dye. For example, the solution may include not greater than 3 wt % of a colorant.

The odor neutralizing solution may also include quaternary ammonium salts. An exemplary quaternary ammonium salts includes benzalkonium chloride, alkyl dimethyl benzyl ammonium chloride, alkyl alkoxyl diethylammonium dihydrogen phosphate, diallyl dimethyl ammonium acetate, or any combination thereof. The quaternary ammonium salt may be included in amount of not greater than 5 wt %, not greater than 4 wt %, or even not greater than 3 wt % based on the total weight of the odor neutralizing solution.

It has been found that the odor neutralizing solution is particularly good at drawing malodorous compounds, such as nitrogenous compounds, away from a surface and binding to them below the surface of a porous material. For example, such malodors can originate from sources such as cooked-fish, pet urine, garbage, smoked-tobacco residue, bathroom smells, natural alkaloids or other amine sources. While the odor neutralizing solution may include fragrances, the odor neutralizing solution can consist essentially of a mixture of components that in combination draw malodors away from a surface and bind to them away from the surface, such as a combination of an organic acid, a surfactant, an organic ester, and an ethylene glycol ether, and optionally a polymer.

In an additional embodiment, an aqueous biocidal composition can be used. For example, the biocidal composition can be applied before or after the preventative solution or the odor neutralizing solution. In an example, the biocidal composition includes a quaternary ammonium salt, an alcohol, an oxidizer, and optionally surfactant or a pH adjuster.

The aqueous biocidal composition can include quaternary ammonium salts. An exemplary quaternary ammonium salts includes benzalkonium chloride, alkyl dimethyl benzyl ammonium chloride, alkyl alkoxyl diethylammonium dihydrogen phosphate, diallyl dimethyl ammonium acetate, or any combination thereof. The quaternary ammonium salt may be included in amount of not greater than 10 wt %, not greater than 8 wt %, or even not greater than 5 wt % based on the total weight of the preventative solution. For example, the quaternary ammonium salt can be included in an amount in a range of 0.1 wt % to 5 wt %, such as a range of 0.3 wt % to 2.0 wt %.

In addition, the aqueous biocidal composition can include an alcohol, such as a low molecular weight alcohol. For example, the alcohol may include an alcohol having between 2 and 6 carbons, such as between 2 and 4 carbons. In an example, the alcohol is ethanol. In another example, the alcohol is isopropyl alcohol. The alcohol may be present in the solution in an amount of 0.1 wt % to 5 wt % based on the total weight of the preventative solution, such as an amount of 0.5 wt % to 5 wt %, an amount of 0.5 wt % to 3 wt %, or amount of 0.5 wt % to 2 wt % based on the total weight of the preventative solution.

In a further example, the aqueous biocidal composition can include an oxidizer. An exemplary oxidizer includes chlorine dioxide. The oxidizer can be included in an amount in a range of 0.05 wt % to 2 wt %, such as a range of 0.05 wt % to 1 wt %, or a range of 0.1 wt % to 0.5 wt %.

In a further example, the aqueous biocidal composition includes a surfactant, such as in an amount of 0.1 wt % to 35 wt % based on the total weight of the biocidal composition. For example, the surfactant may be present in an amount of 0.1 wt % to 10 wt %, such as an amount of 1 wt % to 10 wt %, an amount of 5 wt % to 10 wt %, or an amount of 6 wt % to 9 wt % based on the total weight of the biocidal composition. Alternatively, the surfactant may be present in an amount of 1 wt % to 4 wt %, such as an amount of 1 wt % to 3 wt % based on the total weight of the biocidal composition. Further, the surfactant may be included in amount relative to the organic ester, such as at a ratio of surfactant to organic ester in a range of 1:1 to 5:1, such as a range of 2:1 to 5:1, or even a range of 3:1 to 4:1.

In an example, the surfactant includes alpha olefin sulfonate (AOS), aliphatic ether sulfates (AES), alcohol sulfates (AS), linear alkylbenzenesulfonate (LAS), secondary alkyl sulfonate (e.g., Hostapur™ SAS 30), ethoxylated alcohols such as Neodol™ or Tamadol™, phenoxypolyethoxylethanol, such as octyl or nonyl phenoxypolyethoxylethanol (Tergitol™), alkyl ether phosphonate (e.g., Surfonic®), a phosphonate anionic surfactant, such as poly(oxy-1,2-ethanediyl) alpha-phosphono-omega-(methylphenoxy)-dipotassium (e.g., Rhodafac™ H66), natural surfactants, or any combination thereof. In an example, the surfactant is a nonionic surfactant, an anionic surfactant, a polymeric surfactant, a cationic surfactant or any combination thereof. In particular, the surfactant may be a nonionic surfactant. An exemplary nonionic surfactant includes ethylene oxide or propylene oxide derivatives, such as an ethoxylate ether surfactant. In a particular example, the surfactant includes phenoxypolyethoxylethanol, such as octyl or nonyl phenoxypolyethoxylethanol. In another example, the nonionic surfactant includes ethoxyl-propoxyl terpene, such as Rhodoclean™ EFC. In another example, the surfactant is an anionic surfactant. An exemplary anionic surfactant includes a sulfate or sulfonate surfactant. In an additional example, the surfactant is a natural surfactant, such as a naturally-derived decyl-glucoside sorbitan oleate crosspolymer. In a further example, the surfactant may be a cationic surfactant. Some cationic surfactants are effective at eliminating coliform bacteria or neutralize odors. An exemplary cationic surfactant includes soyethyl morpholinium ethosulfate.

In addition, the aqueous biocidal composition can include a pH adjuster, such as an acid, base, or salt thereof. In a particular example, the pH adjuster can be a bicarbonate. For example, the pH adjuster can be included in an amount of 0.1% to 10% by weight, such as an amount of 0.1% to 5% or an amount of 0.2% to 3% by weight.

In an additional embodiment, an aqueous insecticidal composition can be used. For example, the insecticidal composition can be applied before or after the preventative solution or the odor neutralizing solution. In an example, the insecticidal composition includes a quaternary ammonium salt, an alcohol, an oxidizer, and optionally surfactant or a pH adjuster.

The aqueous insecticidal composition can include quaternary ammonium salts. An exemplary quaternary ammonium salts includes benzalkonium chloride, alkyl dimethyl benzyl ammonium chloride, alkyl alkoxyl diethylammonium dihydrogen phosphate, diallyl dimethyl ammonium acetate, or any combination thereof. The quaternary ammonium salt may be included in amount of not greater than 10 wt %, not greater than 8 wt %, or even not greater than 5 wt % based on the total weight of the preventative solution. For example, the quaternary ammonium salt can be included in an amount in a range of 0.1 wt % to 5 wt %, such as a range of 0.3 wt % to 4.0 wt %.

In a further example, the aqueous insecticidal composition can include an insecticide. An exemplary insecticide includes boric acid. The insecticide can be included in an amount in a range of 0.05 wt % to 5 wt %, such as a range of 0.05 wt % to 3 wt %, or a range of 0.1 wt % to 2.5 wt %.

In a further example, the insecticidal composition includes a surfactant or solubilizer, such as in an amount of 0.1 wt % to 35 wt % based on the total weight of the insecticidal composition. For example, the surfactant may be present in an amount of 0.1 wt % to 10 wt %, such as an amount of 1 wt % to 10 wt %, an amount of 5 wt % to 10 wt %, or an amount of 6 wt % to 9 wt % based on the total weight of the insecticidal composition. Alternatively, the surfactant may be present in an amount of 1 wt % to 4 wt %, such as an amount of 1 wt % to 3 wt % based on the total weight of the insecticidal composition. Further, the surfactant may be included in amount relative to the organic ester, such as at a ratio of surfactant to organic ester in a range of 1:1 to 5:1, such as a range of 2:1 to 5:1, or even a range of 3:1 to 4:1.

In an example, the surfactant includes alpha olefin sulfonate (AOS), aliphatic ether sulfates (AES), alcohol sulfates (AS), linear alkylbenzenesulfonate (LAS), secondary alkyl sulfonate (e.g., Hostapur™ SAS 30), ethoxylated alcohols such as Neodol™ or Tamadol™, phenoxypolyethoxylethanol, such as octyl or nonyl phenoxypolyethoxylethanol (Tergitol™), alkyl ether phosphonate (e.g., Surfonic®), a phosphonate anionic surfactant, such as poly(oxy-1,2-ethanediyl) alpha-phosphono-omega-(methylphenoxy)-dipotassium (e.g., Rhodafac™ H66), polyethylene glycol (PEG) esters derived from oils (e.g., Jeechem FS-102), natural surfactants, or any combination thereof. In an example, the surfactant is a nonionic surfactant, an anionic surfactant, a polymeric surfactant, a cationic surfactant or any combination thereof. In particular, the surfactant may be a nonionic surfactant. An exemplary nonionic surfactant includes ethylene oxide or propylene oxide derivatives, such as an ethoxylate ether surfactant. In a particular example, the surfactant includes phenoxypolyethoxylethanol, such as octyl or nonyl phenoxypolyethoxylethanol. In another example, the nonionic surfactant includes ethoxyl-propoxyl terpene, such as Rhodoclean™ EFC. In an additional example, the surfactant includes PEG esters of hydrogenated natural oils, such as PEG esters of hydrogenates castor oil. In another example, the surfactant is an anionic surfactant. An exemplary anionic surfactant includes a sulfate or sulfonate surfactant. In an additional example, the surfactant is a natural surfactant, such as a naturally-derived decyl-glucoside sorbitan oleate crosspolymer. In a further example, the surfactant may be a cationic surfactant. Some cationic surfactants are effective at eliminating coliform bacteria or neutralize odors. An exemplary cationic surfactant includes soyethyl morpholinium ethosulfate.

In addition, the aqueous insecticidal composition can include glutaraldehyde in an amount of 0.01% to 5%, such as an amount of 0.05% to 2%, or an amount of 0.1% to 2% by weight.

Further, the aqueous insecticidal composition can include insect repellants, such as natural oils. For example, the insect repellant can include citronella, lemongrass, thyme, neem, cedar wood, tea tree, peppermint, or a combination thereof. The repellant can be included in an amount of 0.01% to 5%, such as an amount of 0.05% to 4% or an amount of 0.01% to 3% by weight.

Figure 2:
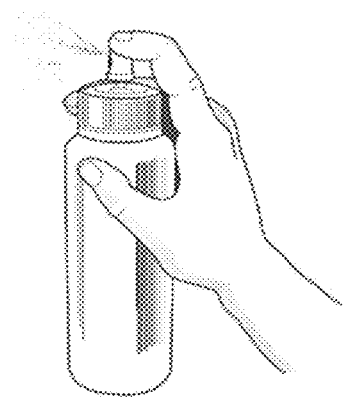
FIG. 2 includes an illustration of an exemplary aerosol spray.

Any one of the preventative solution, the odor neutralizing solutions, the biocidal composition, or the insecticidal composition can be applied as a spritz, aerosol or fog. Alternatively, the preventative solution, the odor neutralizing solutions, the biocidal composition, or the insecticidal composition can be applied using cloth or sponge. For example, the solution or composition can be included in a spray bottle, as illustrated in FIG. 1, or can be included in a pressurized aerosol can, as illustrated in FIG. 2. The spray bottle illustrated in FIG. 1 is an ambient pressure spray bottle that, when motivated, forces the aqueous solution through a nozzle causing a spray that may be applied to a surface.

In another example, the solutions or the compositions may be included in an aerosol pressurized can as illustrated in FIG. 2. The solution may be maintained under pressure by employing compressed propellant gases such as propane, nitrogen, fluorocarbon, or other gases, or any combination thereof.

The preventative solution may be applied to hard surfaces such as natural stone countertops, including granite or marble countertops, Micarta or other vinyl finishes, glass surfaces, or polymeric surfaces. In another example, the preventative solution may be applied to drapes, fabrics, carpeting, upholstery, clothes, bedding, or other articles and surfaces. In particular, the preventative solution may be applied to surfaces found on the interiors of automobiles. In a further example, the preventative solution may be applied to furniture, workbenches, or other hard surfaces. Further, the preventative solution can be used in a medical facility, such as a hospital, emergency room, or clinic.

The odor neutralizing solution, biocidal composition, or insecticidal composition may also be applied on various surfaces. It has been found that the odor neutralizing solution is particularly beneficial for use with surfaces that are porous as the odor neutralizing solution can trap or bind to malodorous compounds, such as amine compounds, and transport them away from a surface into a porous material. In particular, the odor neutralizing solution is particularly advantageous at treating cloth seats, carpets, overhead materials, and other surfaces within an automobile. Further, it is capable of neutralizing malodorous amines or other nuisance nitrogenous odors (including fish odors, latent tobacco amines and alkaloids). Amine odor sources may include marine-originating food odors, pet odors, odors that arise from slow-release of substance-entrained components in fabrics contaminated by use of ember-type tobacco products, such as cigarettes or cigars, garbage, trash, bathroom emissions or other nitrogenous sources of odor.

PREVENTATIVE SOLUTION EXAMPLES

Example 1

Mix titanium dioxide crystal colloid liquid at neutral pH with an emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 2

Mix titanium dioxide crystal colloid liquid at neutral pH with an emulsified polymer. Mix thoroughly and apply to any hard surface, or cloth, fabric, upholstery or other surface. The mixing ratios of ingredients are 3% $TiO_2$ colloid liquid, 10% emulsified polymer, 1% light alcohol (ethyl or IPA) and 86% water.

Example 3

Mix titanium dioxide crystal colloid liquid at pH of 8.0 (adjusted with bicarbonate) with emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 4

Add titanium dioxide crystal colloid liquid at pH of 9.0 (adjusted with sodium bicarbonate) to emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 5

Mix titanium dioxide crystal colloid liquid preferably "S5-300B," at pH of 9.5 (adjusted with sodium carbonate) with emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 6

Add titanium dioxide crystal colloid liquid, which is approximately 18% active, at neutral pH to emulsified polymer. Mix thoroughly and apply to any hard surface, or cloth, fabric, upholstery or other surface. The mixing ratios of ingredients are 4% $TiO_2$ colloid liquid, 9% emulsified polymer, 1% light alcohol (ethyl or IPA) and 86% water.

Example 7

Add emulsified polymer to the titanium dioxide crystal colloid liquid, which is approximately 18% active. Do so at neutral pH. Apply mixture to any hard surface, cloth, fabric, upholstery or other surface. The mixing ratios of ingredients are 4% $TiO_2$ colloid liquid, 9% emulsified polymer, 1% light alcohol (ethyl or IPA) and 86% water.

Example 8

Mix titanium dioxide crystal colloid liquid, at neutral pH with emulsified PEG polymer. The mixing ratios of ingredients are 2% $TiO_2$ colloid liquid, 9% emulsified polymer, 1% light alcohol (ethyl or IPA) and 88% water.

Example 9

Mix titanium dioxide crystal colloid liquid at neutral pH with emulsified PPG (polypropylene glycol) polymer. The mixing ratios of ingredients are 2% $TiO_2$ colloid liquid, 9% emulsified polymer, 1% light alcohol (ethyl or IPA) and 88% water.

Example 10

Add emulsified polymer, such as polyacrylic emulsion, to 18%-active titanium dioxide colloid liquid at a pH of between 7.0 and 8.0. Apply mixture to any surface area. The mixing ratios of ingredients are 3% $TiO_2$ colloid liquid, 10% of the emulsified polyacrylic, 1% light alcohol (ethyl or IPA) and 86% water.

Example 11

Add emulsified polymer, such as polyacrylic emulsion, to 18%-active titanium dioxide colloid liquid at a pH of 9.0. Apply mixture to any surface area. The mixing ratios of ingredients are 3% $TiO_2$ colloid liquid, 10% of the emulsified polyacrylic, 1% light alcohol (ethyl or IPA) and 86% water.

Example 12

Mix titanium dioxide crystal colloid liquid at neutral pH with emulsified polymer. Mix thoroughly and apply to any hard surface, or cloth, fabric, upholstery or other surface. The mixing ratios of ingredients are 4% $TiO_2$ colloid liquid, 15% emulsified polymer, 1% light alcohol (ethyl or IPA) and 80% water.

Example 13

Mix titanium dioxide crystal colloid liquid at neutral pH with emulsified polymer. Mix thoroughly and apply to any hard surface, or cloth, fabric, upholstery or other surface. The mixing ratios of ingredients are 6% $TiO_2$ colloid liquid, 8% emulsified polymer, 4% light alcohol (ethyl or IPA) and 82% water.

EXAMPLE 14.

Mix titanium dioxide crystal colloid liquid at pH of 12.0 with emulsified PPG (polypropylene glycol) polymer. The mixing ratios of ingredients are 2% $TiO_2$ colloid liquid, 9% emulsified polymer, 1% light alcohol (ethyl or IPA) and 88% water.

Example 15

Mix titanium dioxide crystal colloid liquid at pH of 12.0 with emulsified polymer. Mix thoroughly and apply to any hard surface, or cloth, fabric, upholstery or other surface. The mixing ratios of ingredients are 2% $TiO_2$ colloid liquid, 9% emulsified polymer, 1% light alcohol (ethyl or IPA) and 88% water.

Example 16

Mix titanium dioxide crystal colloid liquid at neutral pH with emulsified polymer. Mix thoroughly and apply to any hard surface, or cloth, fabric, upholstery or other surface. The mixing ratios of ingredients are 6% $TiO_2$ colloid liquid, 12% emulsified polymer, 4% light alcohol (ethyl or IPA) and 78% water.

Example 17

Mix titanium dioxide crystal colloid liquid at neutral pH with emulsified polymer. Mix thoroughly and apply to any hard surface, or cloth, fabric, upholstery or other surface. The mixing ratios of ingredients are 6% $TiO_2$ colloid liquid, 14% emulsified polymer, 5% light alcohol (ethyl or IPA) and 75% water.

Example 18

Add emulsified polymer, such as PEG emulsion, to 18%-active titanium dioxide colloid liquid at a pH of between 7.0 and 8.0. Apply mixture to any surface area. The mixing ratios of ingredients are 3% $TiO_2$ colloid liquid as detailed above, 10% of the emulsified PEG, 1% light alcohol (ethyl or IPA) and 86% water.

Example 19

Add emulsified polymer, such as PPG (polypropylene glycol) polyacrylic copolymer emulsion, to 18%-active titanium dioxide colloid liquid a neutral pH. Apply mixture to any surface area. The mixing ratios of ingredients are 3% $TiO_2$ colloid liquid as detailed above, 10% of the emulsified polyacrylic, 1% light alcohol (ethyl or IPA) and 86% water.

Example 20

Mix titanium dioxide crystal colloid liquid at a pH of 9.5 with emulsified polymer. Mixing ratios of ingredients are 4% $TiO_2$ colloid liquid, 15% emulsified polymer, 1% light alcohol (ethyl or IPA) and 80% water.

Example 21

Mix titanium dioxide crystal colloid liquid at pH 10.0 with emulsified latex polyamide. The mixing ratios of ingredients are 6% $TiO_2$ colloid liquid, 8% emulsified polymer, 4% light alcohol (ethyl or IPA) and 82% water.

Example 22

Mix titanium dioxide crystal colloid liquid at pH of 12.0 with emulsified polyamide. The mixing ratios of ingredients are 2% $TiO_2$ colloid liquid, 9% emulsified polyamide, 1% IPA (isopropyl alcohol) and 88% water.

Example 23

Add emulsified polymer, such as PVA (partially hydrolyzed polyvinyl acetate) emulsion, to 18%-active titanium dioxide colloid liquid at a pH of between 7.0 and 8.0. Apply mixture to any surface area. The mixing ratios of ingredients are 3% $TiO_2$ colloid liquid, 10% of the emulsified PVA, 1% light alcohol (ethyl or IPA) and 86% water.

Example 24

Figure 3:
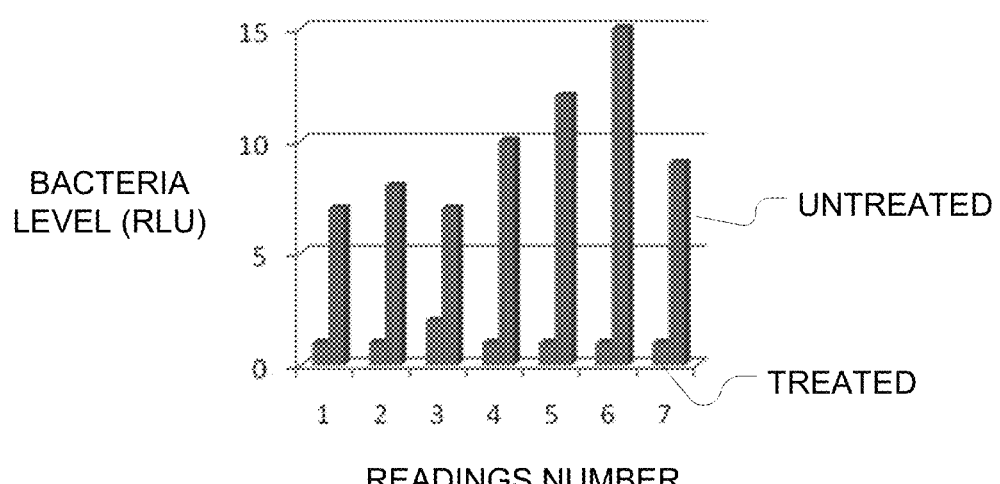
FIG. 3, FIG. 4, and FIG. 5 include graph illustrations of deodorizer performance.
Figure 4:
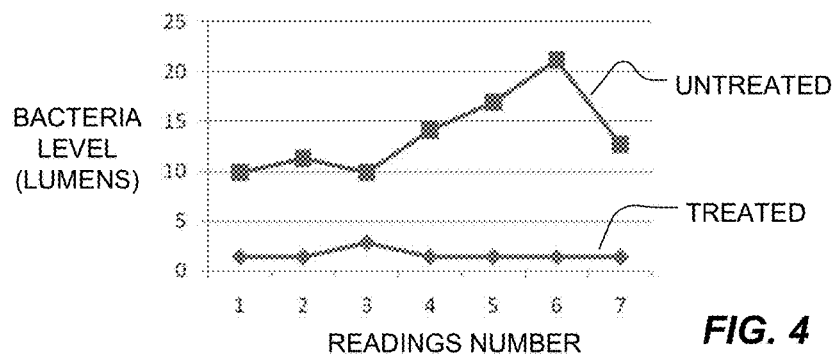

The preventative solution of Example 10 is applied to surfaces and tested for activity against bacterial growth. After 17 minutes under uniform artificial light (254 nm), the bacteria levels are measured in relative light units (RLUs). As illustrated in FIG. 3, the treated surfaces exhibit significantly lower bacterial activity. Similar results are seen when measured in lumens, as illustrated in FIG. 4.

Figure 5:
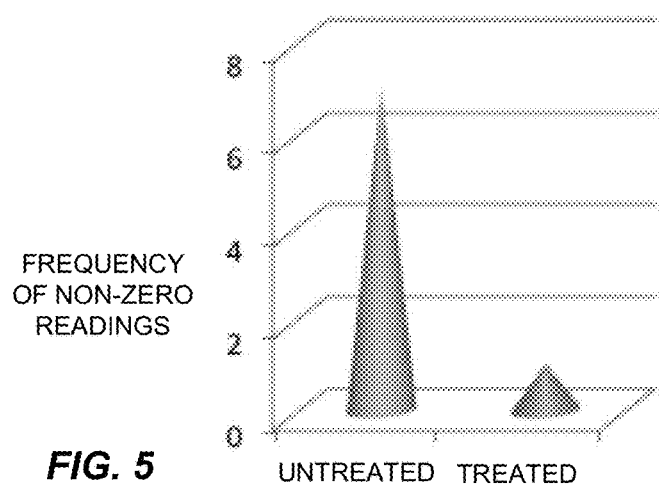

Elimination of bacteria is measured based on the presence of adenosine triphosphate (ATP). As illustrated in FIG. 5, the number of bacterial colonies is significantly fewer when treated with the preventative solution.

ODOR NEUTRALIZING SOLUTION EXAMPLES

Example 1

An aqueous mix of ethyl butyrate and Tergitol® in effective emulsifying proportions (between 3:1 and 4:1 Tergitol®:ethyl butyrate) with a quaternary ammonium salt and a fragrance is formed.

Example 2

An aqueous mix of methyl salicylate and Tergitol® in effective emulsifying proportions (between 3:1 and 4:1 Tergitol®:methyl salicylate) with a quaternary ammonium salt and a fragrance is formed.

Example 3

A mixture of ethyl butyrate, or methyl butyrate, and C-550 in effective emulsifying proportions (between 3:1 and 4:1 C-550:ethyl butyrate) is prepared. A second solution is prepared to also include a quaternary ammonium salt and a fragrance.

Example 4

The aqueous mix of methyl butyrate and alcohol sulfate in effective emulsifying proportions (between 3:1 and 4:1 alcohol sulfate:methyl butyrate) is prepared.

Example 5

An aqueous mix of ethyl valerate and methyl ester sulfonate in effective emulsifying proportions (between 3:1 and 4:1 methyl ester sulfonate:ethyl valerate) is prepared. A second solution is prepared to also include a quaternary ammonium salt or a fragrance.

Example 6

An aqueous mix of methyl butyrate and Tergitol® in effective emulsifying proportions (between 3:1 and 4:1 Tergitol®:methyl butyrate) is prepared. A second solution is prepared to additionally include a quaternary ammonium salt ingredient and a fragrance.

Example 7

An aqueous mix of methyl butyrate and alcohol sulfate in effective emulsifying proportions (between 3:1 and 4:1 alcohol sulfate:methyl butyrate) is prepared.

Example 8

An aqueous mix of ethyl amylate and succinate surfactant (between 3:1 and 4:1 succinate surfactant:ethyl amylate) is prepared.

Example 9

Mix of an organic ester and a surfactant selected from AOS, AS AES, LAS, Neodol, Surfonic, Tergitol, or Naturals is prepared. A second solution is prepared to additionally include a quaternary ammonium salt ingredient or a fragrance.

Example 10

A solution is prepared that includes the mixture of Example 9 and propionate and acetate derivatives.

Example 11

An aqueous mix of methyl butyrate and alcohol sulfate in effective emulsifying proportions (between 3:1 and 4:1 alcohol:methyl butyrate) is prepared.

Example 12

Propionate and acetate derivatives are mixed with methyl butyrate and Tomadol™ in effective emulsifying proportions. A second solution is prepared to also include a quaternary ammonium salt ingredient or a fragrance.

Example 13

A mixture of ethyl butyrate, or methyl butyrate, and C-550 in effective emulsifying proportions (between 3:1 and 4:1 C-550:methyl/ethyl butyrate) is prepared. As second solution is prepared to also include a quaternary ammonium salt ingredient or a fragrance.

Example 14

An aqueous mix of ethyl amylate and MES (between 3:1 and 4:1 MES:ethyl amylate) is prepared. A second solution is prepared to also include a quaternary ammonium salt or a fragrance.

Example 15

A water mix of methyl salicylate, or similar ester, and surfactant is prepared.

Example 16

An aqueous mix of butyrate or hexanoate esters with alcohol sulfate in effective emulsifying proportions (between 3:1 and 4:1 alcohol sulfate:butyrate or hexanoate) is prepared.

Example 17

A mixture including hexanoate and propionate and acetate derivatives are prepared.

Example 18

An aqueous mix of AES or AS and low-molecular weight organic acid esters is prepared.

Example 19

An aqueous mix of esters and a cationic surfactant in effective emulsifying proportions (between 3:1 and 4:1 cationic surfactant:organic ester), a quaternary ammonium salt ingredient and a fragrance is prepared.

Example 20

A mixture of an organic ester, a surfactant and a colorant is prepared.

Example 21

A solution is prepared to include the solution of Example 1 and a cellosolve ether.

Example 22

A solution is prepared to include the solution of Example 2 and a Cellosolve ether.

Example 23

A solution is prepared to include the solution of Example 3 and a Cellosolve ether.

Example 24

A solution is prepared to include the solution of Example 4 and a Cellosolve ether.

Example 25

A solution is prepared to include the solution of Example 5 and a Cellosolve ether.

Example 26

A solution is prepared to include the solution of Example 6 and a Cellosolve ether.

Example 27

A solution is prepared that includes an aqueous base, 5 wt % citric acid, 3 wt % ethyl butyrate, 9 wt % Tergitol, 3 wt % Cellosolve, 0.3 wt % fragrance, 0.75 wt % of an acrylate polymer, and 0.4 wt % dye.

Example 28

A solution is prepared that includes an aqueous base, 5 wt % citric acid, 3 wt % ethyl acetate, 3 wt % aldehyde, 9 wt % Tergitol, 3 wt % Cellosolve, 0.3 wt % fragrance, 0.75 wt % of an acrylate polymer, and 0.4 wt % dye.

Example 29

A solution is prepared that includes an aqueous base, 5 wt % citric acid, 3 wt % ethyl butyrate, 3 wt % aldehyde, 9 wt % Tergitol, 3 wt % Cellosolve, 0.3 wt % fragrance, 0.75 wt % of an acrylate polymer, and 0.4 wt % dye.

Figure 6:
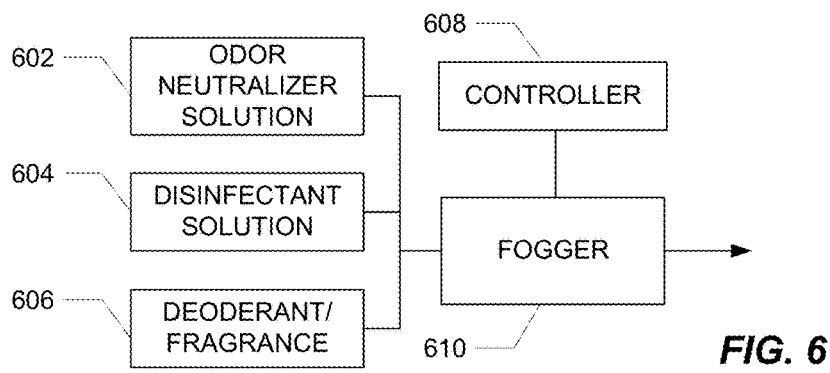
FIG. 6 includes an illustration of an exemplary system and method for treating a space.

In a further example, the solutions can be applied through a fogger to generate a fog of droplets. The fogger can be operated manually, automatically, or semi-automatically. In a particular example, a fogger device, such as illustrated in FIG. 6, can be used. The fogger device can include two or more containers (602, 604, or 606), such as at least three containers to store solutions. The fogger 610 can generate a fog from each of the solutions having a droplet size in the range of 0.1 micrometers to 100 micrometers, such as a range of 0.1 micrometers to 50 micrometers, or even a range of 1 micrometer to 20 micrometers. For example, the fogger can use an ultrasonic fog generator, such as a piezoelectric fog generator.

A controller 608 can be programmed to sequentially fog one or more of the solutions for a period of time using a fogger 610 coupled to the controller 608 and in fluid communication with the containers (602, 604, or 606). For example, the controller 608 can be programmed to fog a select solution for a select period of time. In another example, the controller 608 can be programmed to generate fog based on moisture (e.g., humidity), either separately or in cooperation with timing. For example, the controller 608 can be programmed to maintain a humidity of greater than 80%, such as greater than 90%, or even greater than 95%, for a select period of time using a select solution. The order, timing, and humidity can be set using input to the controller 608.

In a particular example, an odor neutralizing solution 602 can be fogged for a first period of time. The odor neutralizing solution can have the composition described above. Subsequently, a disinfectant solution 604, such as the biocidal composition or the insecticidal composition, can be fogged for a second period of time, followed by fogging of the preventative solution 606 for a third period of time. The disinfectant solution 604 can include an oxidizer and quaternary ammonium, such as described above and may or may not be used in the amounts described above. The preventative solution 606 can have the composition described above. In an example, the length of fogging any of the solutions can be determined based on the size of the space (volume or area) to be treated. For example, each of the solutions can be fogged for a period in a range of 1 minute to 1 hour, such as a range of 5 minutes to 30 minutes or a range of 10 minutes to 30 minutes.

In a first aspect, a preventative solution includes an aqueous base, 1 wt % to 6 wt % titanium dioxide having an average particle size of not greater than 100 nm, 0.5 wt % to 20 wt % alcohol having 2 to 4 carbons, and 3 wt % to 15 wt % of a binding agent.

In an example of the first aspect, the average particle size is not greater than 60 nm. In another example, the average particle size is at least 3 nm.

In a further example of the first aspect and the above examples, titanium dioxide is included in an amount of 2 wt % to 6 wt %.

In an additional example of the first aspect and the above examples, the alcohol includes isopropyl alcohol.

In another example of the first aspect and the above examples, the binding agent includes a wax.

In a further example of the first aspect and the above examples, the wax includes a fatty acid ester of a sterol.

In an additional example of the first aspect and the above examples, the binding agent includes a polymer.

In another example of the first aspect and the above examples, the binding agent is included in an amount in a range of 8 wt % to 15 wt %.

In a further example of the first aspect and the above examples, the preventative solution further includes a surfactant in an amount of 0.3 wt % to 9 wt %. For example, the surfactant can include a monoether of polyethylene glycol. In particular, the polyethylene glycol can include between 3 and 10 ethylene glycol units.

In an additional example of the first aspect and the above examples, the preventative solution further includes a quaternary ammonium salt in an amount in a range of 0.1 wt % to 2 wt %.

In another example of the first aspect and the above examples, the preventative solution further includes an oxidizer in an amount in a range of 0.05 wt % to 2 wt %. For example, the oxidizer can include chlorine dioxide.

In a further example of the first aspect and the above examples, the preventative solution further includes an antifungal agent in an amount in a range of 0.01 wt % to 0.5 wt %.

In a second aspect, a preventative solution includes an aqueous base, 1 wt % to 6 wt % titanium dioxide having an average particle size of not greater than 100 nm, 0.5 wt % to 20 wt % alcohol having between 2 and 4 carbons, 3 wt % to 15 wt % wax binding agent, the wax comprising a fatty acid ester of a sterol, 0.3 wt % to 9 wt % surfactant comprising a monoether of a polyethylene glycol having between 3 and 10 ethylene glycol units, 0.1 wt % to 2 wt % quaternary ammonium salt, 0.01 wt % to 0.5 wt % isothiazolinone agent, and 0.05 wt % to 2 wt % chlorine dioxide.

In a third aspect, a method of treating an area includes fogging a disinfectant solution using the automated aerosolizing device for a first period of time. The disinfectant solution includes an oxidizer and quaternary ammonium salt. The method further includes fogging a preventative solution using an automated aerosolizing device for a subsequent second period of time. The preventative solution includes an aqueous base, 1 wt % to 6 wt % titanium dioxide having an average particle size of not greater than 100 nm, 0.5 wt % to 20 wt % alcohol having between 2 and 4 carbons, 3 wt % to 15 wt % wax binding agent, the wax comprising a fatty acid ester of a sterol, and 0.3 wt % to 9 wt % surfactant comprising a monoether of a polyethylene glycol having between 3 and 10 ethylene glycol units.

In an example of the third aspect, the preventative solution further includes 0.1 wt % to 2 wt % quaternary ammonium salt, 0.01 wt % to 0.5 wt % isothiazolinone agent, and 0.05 wt % to 2 wt % chlorine dioxide.

In another example of the third aspect and the above example, the method further includes fogging an odor neutralizer solution prior to fogging the disinfectant solution. The odor neutralizer solution includes an aqueous base, 0.1 wt % to 10 wt % of an organic acid, 0.1 wt % to 35 wt % of a surfactant, 0.1 wt % to 10 wt % of an organic ester, and 0.1 wt % to 11 wt % of an ethylene glycol ether.

In another aspect, a method treating an area includes fogging an odor neutralizing solution using an automated aerosolizing device for a first period of time. The odor neutralizing solution includes an aqueous base; 0.1 wt % to 10 wt % of an organic acid; 0.1 wt % to 35 wt % of a first surfactant; and 0.1 wt % to 10 wt % of an organic ester derived from a carboxylic acid having at least 4 carbons. The method further includes fogging a preventative solution using an automated aerosolizing device for a subsequent second period of time. The preventative solution includes an aqueous base; 1 wt % to 6 wt % titanium dioxide having an average particle size of not greater than 100 nm; 0.5 wt % to 20 wt % alcohol having 2 to 4 carbons; a second surfactant in an amount of 0.3 wt % to 9 wt %; and a quaternary ammonium salt in an amount of 0.1 wt % to 2 wt %.

In an example of the above aspects, the odor neutralizing solution further includes 0.1 wt % to 11 wt % of an ethylene glycol ether.

In another example of the above aspects and examples, the odor neutralizing solution includes the organic acid in an amount of 0.1 wt % to 10 wt %.

In a further example of the above aspects and examples, the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof.

In an additional example of the above aspects and examples, the organic acid is citric acid.

In another example of the above aspects and examples, the odor neutralizing solution includes the first surfactant in an amount of 1 wt % to 10 wt %.

In a further example of the above aspects and examples, the first surfactant is a nonionic surfactant. For example, the nonionic surfactant includes an ethoxylate surfactant.

In an additional example of the above aspects and examples, the first surfactant is an anionic surfactant.

In another example of the above aspects and examples, the carboxylic acid includes 4 to 10 carbons.

In a further example of the above aspects and examples, the odor neutralizing solution further includes not greater than 5 wt % of a polymer.

In an additional the method further comprises fogging a sanitizing solution comprising 0.1 wt % to 2 wt % quaternary ammonium salt; 0.01 wt % to 0.5 wt % isothiozolinone agent; and 0.05 wt % to 2 wt % chlorine dioxide.

In another example of the above aspects and examples, the average particle size is not greater than 60 nm.

In a further example of the above aspects and examples, the alcohol includes isopropyl alcohol.

In an additional example of the above aspects and examples, the preventative solution further includes a binding agent wax.

In another example of the above aspects and examples, the preventative solution further includes a binding agent polymer.

In a further example of the above aspects and examples, the preventative solution includes a binding agent in an amount of 0.5 wt % to 3 wt %.

In an additional example of the above aspects and examples, the second surfactant includes a monoester of polyethylene glycol.

In another example of the above aspects and examples, the preventative solution further includes an oxidizer in an amount in a range of 0.05 wt % to 2 wt %.

In a further example of the above aspects and examples, the oxidizer includes chlorine dioxide.

Note that not all of the activities described above in the general description or the examples are required, that a portion of a specific activity may not be required, and that one or more further activities may be performed in addition to those described. Still further, the orders in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of treating an area, the method comprising:
    fogging an odor neutralizing solution using an automated aerosolizing device for a first period of time, the odor neutralizing solution including:
        an aqueous base;
        0.1 wt % to 10 wt % of an organic acid;
        0.1 wt % to 35 wt % of a first surfactant; and
        0.1 wt % to 10 wt % of an organic ester derived from a carboxylic acid having at least 4 carbons; and
    fogging a preventative solution using an automated aerosolizing device for a subsequent second period of time, the preventative solution comprising:
        an aqueous base;
        1 wt % to 6 wt % titanium dioxide having an average particle size of not greater than 100 nm;
        0.5 wt % to 20 wt % alcohol having 2 to 4 carbons;
        a second surfactant in an amount of 0.3 wt % to 9 wt %; and
        a quaternary ammonium salt in an amount of 0.1 wt % to 2 wt %.

2. The method of claim 1, wherein the odor neutralizing solution further includes 0.1 wt % to 11 wt % of an ethylene glycol ether.

3. The method of claim 1, wherein the odor neutralizing solution includes the organic acid in an amount of 0.1 wt % to 10 wt %.

4. The method of claim 1, wherein the organic acid includes ascorbic acid, aspartic acid, citric acid, maleic acid, oxalic acid, succinic acid, glycolic acid, lactic acid, malic acid, tartaric acid, glutaric acid, mandelic acid, malonic acid, adipic acid, phthalic acid, or any combination thereof.

5. The method of claim 4, wherein the organic acid is citric acid.

6. The method of claim 1, wherein the odor neutralizing solution includes the first surfactant in an amount of 1 wt % to 10 wt %.

7. The method of claim 1, wherein the first surfactant is a nonionic surfactant.

8. The method of claim 7, wherein the nonionic surfactant includes an ethoxylate surfactant.

9. The method of claim 1, wherein the first surfactant is an anionic surfactant.

10. The method of claim 1, wherein the carboxylic acid includes 4 to 10 carbons.

11. The method of claim 1, wherein the odor neutralizing solution further includes at least 0.1 wt. % and not greater than 5 wt. % of a polymer.

12. The method of claim 1, further comprising fogging a sanitizing solution comprising:
 0.1 wt % to 2 wt % quaternary ammonium salt;
 0.01 wt % to 0.5 wt % isothiozolinone agent; and
 0.05 wt % to 2 wt % chlorine dioxide.

13. The method of claim 1, wherein the average particle size is not greater than 60 nm.

14. The method of claim 1, wherein the alcohol includes isopropyl alcohol.

15. The method of claim 1, wherein the preventative solution further includes a binding agent wax.

16. The method of claim 1, wherein the preventative solution further includes a binding agent polymer.

17. The method of claim 1, wherein the preventative solution includes a binding agent in an amount of 0.5 wt % to 3 wt %.

18. The method of claim 1, wherein the second surfactant includes a monoester of polyethylene glycol.

19. The method of claim 1, wherein the preventative solution further includes an oxidizer in an amount in a range of 0.05 wt % to 2wt %.

20. The method of claim 19, wherein the oxidizer includes chlorine dioxide.

* * * * *